US006582409B1

(12) United States Patent
Squitieri

(10) Patent No.: US 6,582,409 B1
(45) Date of Patent: *Jun. 24, 2003

(54) HEMODIALYSIS AND VASCULAR ACCESS SYSTEMS

(75) Inventor: Rafael Squitieri, Morristown, NJ (US)

(73) Assignee: GraftCath, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/490,368

(22) Filed: Jan. 24, 2000

Related U.S. Application Data

(63) Continuation of application No. 08/835,316, filed on Apr. 7, 1997, now Pat. No. 6,102,884.
(60) Provisional application No. 60/037,094, filed on Feb. 3, 1997.

(51) Int. Cl.[7] .......................... A61K 9/02; A61M 31/00; A61M 5/00; A61M 37/00
(52) U.S. Cl. ...................... 604/288.01; 604/8; 604/6.16
(58) Field of Search ...................... 604/288.01–288.09, 604/890.1, 891.1, 892.1, 93.01, 264, 523, 7–10; 623/1.1, 1.36, 1.13–1.14; 606/151–159

(56) References Cited

U.S. PATENT DOCUMENTS

| | | | |
|---|---|---|---|
| 3,683,926 A | * 8/1972 | Suzuki | |
| 3,818,511 A | * 6/1974 | Goldberg et al. | 264/257 |
| 4,318,401 A | 3/1982 | Zimmerman | |
| 4,447,237 A | 5/1984 | Frisch et al. | |
| 4,496,349 A | * 1/1985 | Cosentino | 604/175 |
| 4,822,341 A | 4/1989 | Colone | |
| 4,898,669 A | 2/1990 | Tesio | |
| 4,929,236 A | 5/1990 | Sampson | |
| 5,041,098 A | 8/1991 | Loiterman et al. | |
| 5,192,310 A | 3/1993 | Herweck et al. | |
| 5,399,168 A | 3/1995 | Wadsworth, Jr. et al. | |
| 5,476,451 A | 12/1995 | Ensminger et al. | |
| 5,558,641 A | 9/1996 | Glantz et al. | |
| 5,562,618 A | 10/1996 | Cai et al. | |
| 5,591,226 A | 1/1997 | Trerotola et al. | |

(List continued on next page.)

FOREIGN PATENT DOCUMENTS

DE  4418910  7/1995

OTHER PUBLICATIONS

Alan S. Coulson, M.D., Jagjit Singh, M.D., Joseph C. Moya, "Modification of Venous End of Dialysis Grafts: An Attempt to Reduce Neointimal Hyperplasia," *Dialysis & Transplantation*, vol. 29, No. 1, Jan. 2000, pp. 10 to 18.

A.S. Coulson, M.D., Ph.D, Judy Quarnstrom, I.V.N., J. Moshimia, M.D., "A Combination of the Elephant Trunk Anastomosis Technique and Vascular Clips for Dialysis Grafts," *Surgical Rounds*, Nov. 1999, pp. 596 to 608.

*Primary Examiner*—Brian L. Casler
*Assistant Examiner*—Catherine Serke
(74) *Attorney, Agent, or Firm*—Daly, Crowley & Mofford, LLP

(57) ABSTRACT

A hemodialysis and vascular access system which includes a catheter having an arteriovenous fistula utilizing an indwelling silastic venous end and an arterial end which is adapted to be anastomosed to an artery is described. The catheter includes a needle receiving s through which a needle is inserted to access fluid flow within the hemodialysis and vascular access system. The invention enables use of an "arterialized" indwelling venous catheter where blood flows from an artery through the hemodialysis and vascular access system and is returned to the venous system via an arrangement wherein the outflow opening is distinct and distant from the site where the catheter enters the vein. The site of blood return to the venous system is not directly fixed to the venous wall but is free floating within the venous system. This system provides a hemodialysis and venous access graft which has superior longevity and performance and is relatively easy to implant.

18 Claims, 8 Drawing Sheets

U.S. PATENT DOCUMENTS

| | | |
|---|---|---|
| 5,637,088 A | 6/1997 | Wenner et al. |
| 5,637,102 A | 6/1997 | Tolkoff et al. |
| 5,676,346 A | 10/1997 | Leinsing |
| 5,743,894 A | 4/1998 | Swisher |
| 5,755,775 A | 5/1998 | Trerotola et al. |
| 5,792,104 A | 8/1998 | Speckman et al. |
| 5,797,879 A | 8/1998 | DeCampli |
| 5,830,224 A | 11/1998 | Cohn et al. |
| 5,904,967 A * | 5/1999 | Ezaki et al. |
| 6,019,788 A * | 2/2000 | Butters et al. |
| 6,102,884 A * | 8/2000 | Squitieri ............... 604/4.01 |
| 6,156,016 A * | 12/2000 | Maginot ............... 604/264 |
| 6,261,255 B1 * | 7/2001 | Mullis et al. ............ 604/175 |
| 6,338,724 B1 * | 1/2002 | Dossa ............... 604/6.16 |
| 2002/0049403 A1 * | 4/2002 | Alanis ............... 604/8 |

\* cited by examiner

ND VASCULAR ACCESS
HEMODIALYSIS AND VASCULAR ACCESS SYSTEMS

CROSS-REFERENCE TO RELATED APPLICATIONS

This application is a continuation of U.S. application Ser. No. 08/835,316, filed on Apr. 7, 1997 now U.S. Pat. No. 6,102,884 which claims the benefit under 35 U.S.C. §119(e) of U.S. application Ser. No. 60/037,094, filed on Feb. 3, 1997.

BACKGROUND OF THE INVENTION

Currently, HD (hemodialysis) and vascular access for chemotherapy and plasmapheresis is achieved in one of several ways. Applicant's invention involves a new method and instrumentation for HD and vascular access designed to eliminate the problems of the prior methods and create a new, more durable, easier to use, vascular access system.

One prior art method involves a primary arteriovenous fistula. In this method, a native artery is sewn to a native vein creating a high flow system of blood in a vein which over time can be accessed with two hemodialysis needles attached to a dialysis machine. The problem with this method is that few patients are candidates secondary to anatomy and in others the veins or shunt fail to enlarge and mature properly even if the primary fistula remains patent. These arteriovenous fistulas also become aneursymol over time requiring revision.

Another method involves a subcutaneous prosthetic conduit (PTFE) in the shape of a tube which is sewn at either end to openings made in an artery and vein. This method causes recurrent stenosis at the venous outflow leading to thrombosis (i.e., graft closure) secondary to intimal hyperplasia at venous anastomosis. Thrombosis also occurs at needle puncture sites along the PTFE.

Another method involves a "tunneled" percutaneous dual lumen catheter which is inserted into a central vein. This causes recurrent thrombosis secondary to stasis of blood in the lumen (i.e., not a continuous flow system like an A-V fistula) and build up of fibrinous debris at the venous end. Further, the access end of the catheter protrudes through the skin making it cosmetically unappealing, cumbersome to live with, as well as more likely to become infected.

A further method involves the use of the Sorenson Catheter. This is a percutaneous (not tunneled) dual lumen catheter, placed into the central venous system, which is used to provide temporary access for the purposes of hemodialysis. These catheters are prone to kinking, clotting, infection, and poor flow rates.

A still further method of vascular access involves the "Port-a-cath". This system of venous access, which utilizes a subcutaneous reservoir attached to a central venous catheter, is used for long term intervenous access for chemotherapy etc. (It is not intended for HD.) The ports are prone to clotting and must be continually flushed since they are a stagnant system.

Applicant's invention involves a vascular access system, known as the Squitieri Hemodialysis and Vascular Access System, which creates a continuous blood flow and which is easily accessed and resistant to clotting. These advantages provide ideal access for long term HD chemo or blood draws. An example, would be patients who are on coumadin which require weekly blood draws. This new system becomes less painful over time as the skin over the "needle access" site become less sensitive. The veins are spared repeated blood draws which results in vein thrombosis to such a degree that some patients "have no veins left" making routine blood draws impossible.

Among the more relevant prior art patents are U.S. Pat. Nos. 4,898,669, 4,822,341; 5,041,098; and, 4,790,826. None of the foregoing patents disclose a system having the features of this invention. U.S. Pat. No. 4,447,237 describes improvements in a valving slit which includes the provision of a flattened sleeve within an elastomeric body presenting opposed interior surfaces interengaged when the valving slit is in the closed condition and spaced apart when the valving slit is in the open condition.

SUMMARY OF THE INVENTION

A hemodialysis and vascular access system comprises a PTFE end which is sutured to an opening in an artery at one end and the other end is placed into a vein using any technique which avoids the need for an anastomosis between the silicone "venous" end of the catheter and the vein wall. The system comprises any material, synthetic or natural (i.e. vein) which can be sutured to the artery (i.e. preferably PTFE) at one end while the other end is composed of a material which is suitable for placement into a vein in such a way that the openings in the "venous" end of the system are away from the site where the graft enters the vein. The system may also be constructed of multiple layers of materials i.e. PTFE on the inside with silastic on the outside. The "Needle Receiving Site" may also be covered with PTFE to encourage self sealing and tissue in-growth.

A preferred embodiment comprises a combination of PTFE conduit sewn to an artery on one end of the system with the other end connected to a silastic-plastic catheter which can be percutaneously inserted into a vein via an introducer. The venous end may also be placed via open cut down. The seal around the system where it enters the vein may be "self sealing" when placed in percutaneous technique; it may be achieved with a purse string when done by open technique "cut down"; or, it may be sewn to the vein to create a seal with a "cuff" while the system continues downstream within the venous system to return the arterial blood away from the site of entry into the vein. The entire system can be positioned subcutaneously at the completion of insertion. This design is a significant improvement over existing methods because it avoids the most frequent complication of current HD access methods. By utilizing an indwelling venous end, one avoids creating a sewn anastomosis on a vein which is prone to stenosis secondary to neointimal hyperplasia. By having continuous flow through the silastic end of the catheter, thrombosis of these catheters can be avoided. Dialysis is made more efficient by decreasing recirculation of blood which accompanies the use of side by side dual lumen catheters inserted into a central vein. This invention not only benefits the patient but it also speeds dialysis thus saving time and money.

To summarize, the Squitieri Access System comprises a tube composed of PTFE and a silastic catheter. This tube is used to create an arteriovenous fistula. The PTFE end (arterial end) of the tube is sewn to an artery while the silastic catheter end is placed into the venous system by the Seldinger technique much like a standard central line. The entire system is subcutaneous at the completion of insertion. This system is a composite of the arterial end of a "gortex graft" joined to the venous end of a "permacath". This system enjoys strengths of each type of access and at the same time avoids their weaknesses.

Accordingly, an object of this invention is to provide a new and improved vascular access system.

Another object of this invention is to provide a new and improved hemodialysis and vascular access system including an easily replaceable needle receiving site which has superior longevity and performance, is more easily implanted, more easily replaced, and is "user friendly" i.e. easily and safely accessed by a nurse or patient which is ideal for home hemodialysis.

A more specific object of this invention is to provide a new and improved Squitieri hemodialysis and vascular access system including a subcutaneous composite PTFE/Silastic arteriovenous fistula.

A further object of this invention is to provide a new and improved hemodialysis and vascular access system including a fistula utilizing an indwelling silastic end which is inserted percutaneously into the venous system and a PTFE arterial end which is anastomosed to an artery and including a unique needle receiving sites which are positioned anywhere between the ends and which have superior longevity and performance.

A further object of this invention is to provide a system constructed to preserve laminar flow within the system and at the venous outflow end to reduce turbulence and shear force in the vascular system to the degree possible.

A still further object of this invention is to provide a system wherein the arterial end (PTFE) may also be placed by percutaneous technique including one where blood entry holes are distant from the site where blood enters the veins.

BRIEF DESCRIPTION OF THE DRAWINGS

The above and other objects of this invention may be more clearly seen when viewed in conjunction with the accompanying drawings wherein:

FIG. 13 shows holes where ports can be fixed in place while

DETAILED DESCRIPTION OF THE INVENTION

Figure 1:
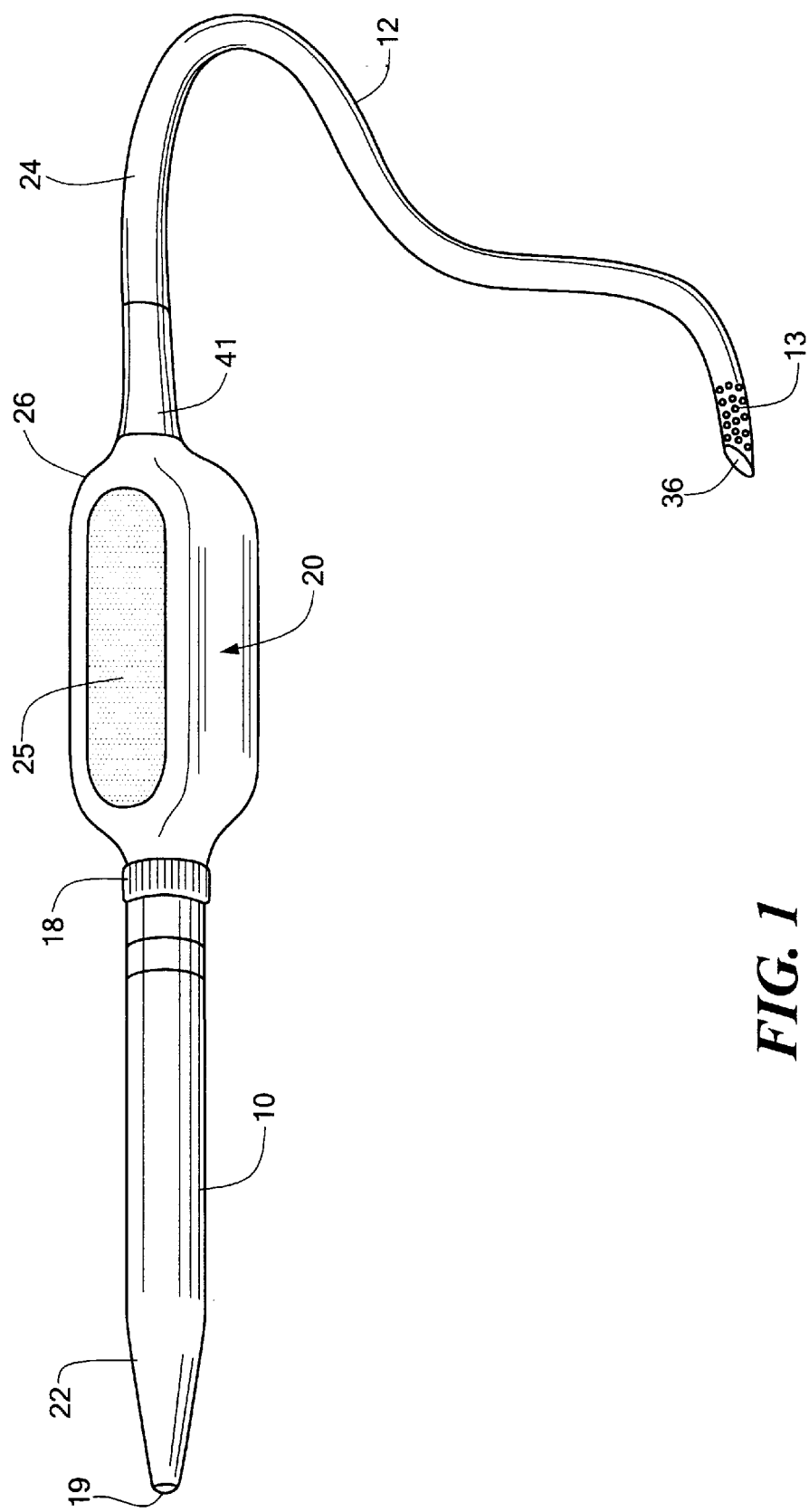
FIG. 1 is a perspective view of the vascular access system comprising the invention.

Referring to the drawings the Squitieri hemodialysis and vascular system, as shown in FIG. 1, comprises a PTFE/Dacron (or other synthetic or natural material) tube 10 of several centimeters in length which is attached at one end by means of a coupling to a needle access site or receiving site 20. Adjustable band 18 regulates the blood flow through the access site 20. The PTFE tube 10 is approximately 7 mm in diameter and transitions downward to an open end portion 19 approximately 4 mm in diameter.

Figure 2:
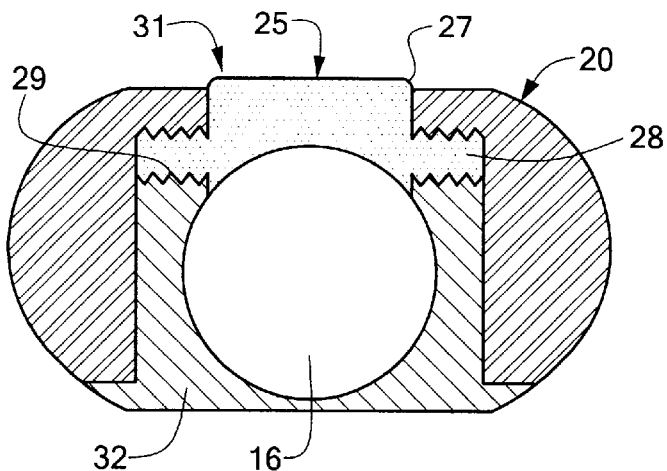
FIG. 2 is a cross-sectional view of the needle access site taken along the line 2—2 of FIG. 1.

The access site 20 includes an in line aperture 16, see FIG. 2, having a silicone tube 41 connected thereto at one end leading to a long flexible plastic/silastic/silicone tube 12 with transverse holes 13 along its free end. The number of holes 13 may vary within predetermined limits to achieve optimum results. The end 36 may be beveled for ease of insertion. This tubular arrangement functions as a subcutaneous connection between the arterial and venous systems. It may also be modified to allow part of the system to exit through the skin 14 (FIG. 3) to provide access to the blood circulation without placing needles 15 (FIG. 3) through the skin 14 into the fistula (usually at the PTFE end).

Along the length of the catheter specially constructed needle access sites 20 (FIGS. 1, 7, 8, and 10) are located to receive specially designed needles 15 into the system to gain access to the blood stream which flows through aperture 16. This method avoids perigraft bleeding which leads to thrombosis either by compression of the graft by hematoma or by manual pressure applied to the graft in an attempt to control the bleeding.

The needle access areas 20 which are designed to receive needles 15 etc. to allow access to the system are in line conduits with self-sealing material 25 which is here shown as a silicone member 25 which can be located beneath the skin surface. The silicone member 25 comprises an oval configuration exposed within the frame 26 for ease of puncture. The system may be accessed immediately after insertion without having to wait for the graft to incorporate into the tissues as is the case with the current methods of subcutaneous fistulas. These access areas 20 will protect the graft since they are uniformly and easily utilized requiring little training or experience. The "needle receiving" sites 20 are designed in such a way to preserve laminar flow as far as possible (i.e. not a reservoir arrangement). Needle receiver sites 20 may be connected to a system via "quick couple" 45 for easy exchangability, see FIG. 11.

Figure 3:
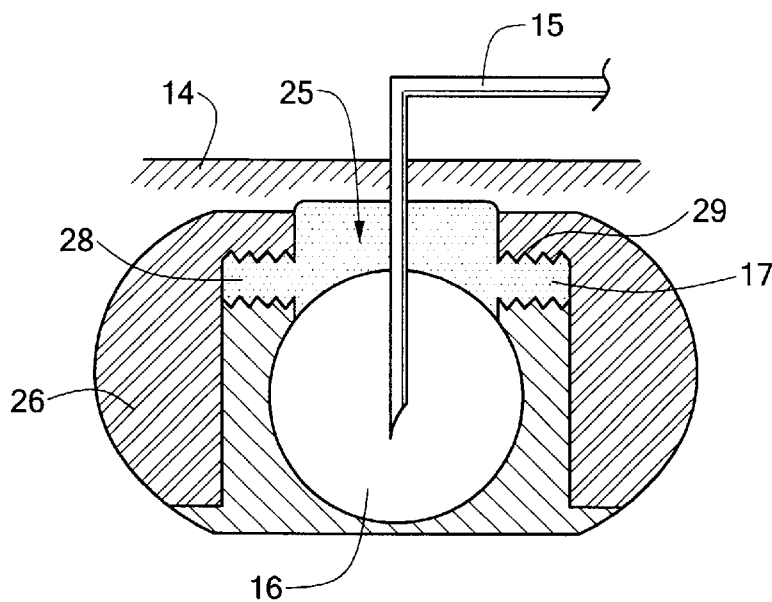
FIG. 3 is a cross-sectional view similar to FIG. 2 with a needle inserted into the access site.

FIGS. 2 and 3 disclose a needle access site 20 wherein a silicone member 25 is mounted within a plastic or metal frame 26. A protruding portion 27 of member 25 extends upwardly through the aperture 31 while a flange portion 28 extends outwardly on both sides of the portion 27 to be gripped by teeth 29 on the internal surface of frame 26 and member 32. The frame 26 includes an in-line aperture or passage 16 through the needle access site 20 for blood flow. The blood flow is accessed by inserting needles 15 through the silicone member 25 which is preferably oval in shape. The teeth 29 seal the arterial pressure. The passage 16 of the needle receiving site 20 is tubular in shape.

Figure 5:
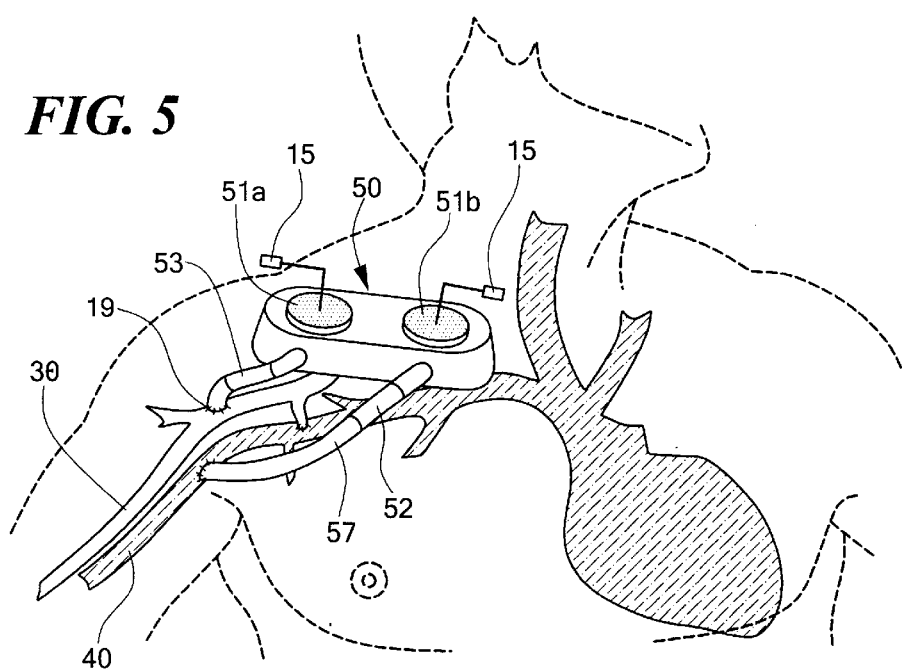
FIG. 5 is a perspective view of an alternate embodiment of the invention with one port having a tube sewn to a vein.
Figure 6:
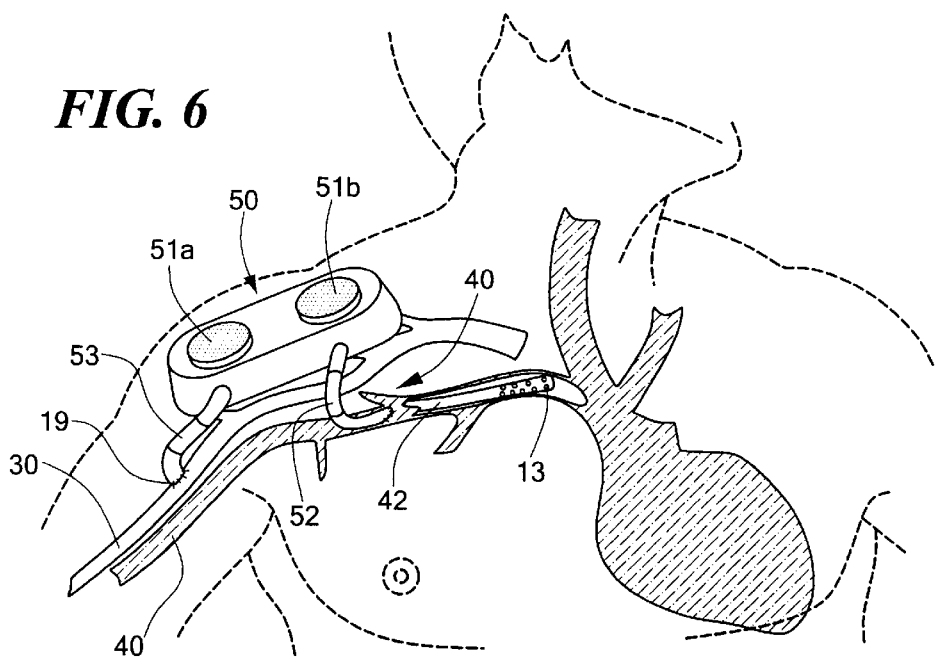
FIG. 6 is a perspective view of the embodiment in FIG. 5 with a silastic tube floated down a vein.

The open end portion 19 of the PTFE tube 10 is sewn to an opening in an artery 30, see FIGS. 5, 6, 7, 8 and 9, while the flexible plastic tube 24 of the system having been inserted percutaneously lies in the venous system in such a way that the openings 13 in the silastic tube 12 are downstream from the site where the flexible plastic tube 24 enters the vein 40 (see FIGS. 5 and 6). The venous end may be inserted via "cutdown". The purpose of the system is to allow communication between an artery 30 and a vein 40 in such a way that the system may be accessed by either puncturing the PTFE segment or by entering the specialized "needle receiving" site 20. This allows blood to flow from the system to a hemodialysis (HD) machine (not shown) and then return into the venous outflow portion at a more distal (venous end) location allowing the blood to return from the HD machine (not shown) back into the patient.

Figure 4:
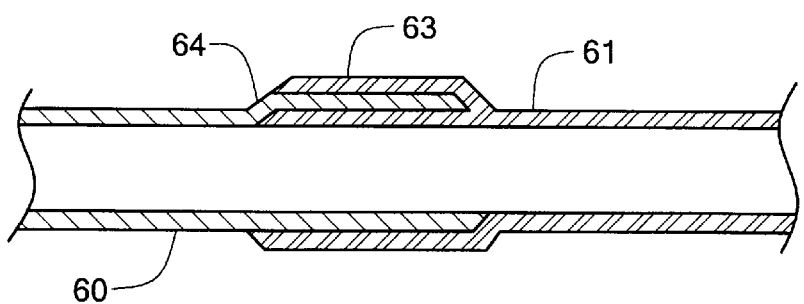
FIG. 4 is a cross-sectional view of the coupling between the PTFE and the silicone venous end of the catheter.

FIG. 4 discloses, as an alternative, a "glued" connection between PTFE tubing 60 and silicone tubing 61 wherein the PTFE tubing 60 is inserted into an enlarged portion of silicone tubing 61 wherein the longitudinally extending portion includes a raised section 63 which locks a raised section 64 of PTFE tubing 61 within the silicone tubing 61.

In this invention, the materials used may vary as specified herein. The system may be constructed of one or more specific materials. The arteries and veins used may also vary. Material may also be covered with thrombus resistant coatings (heparin, etc.) or biologic tissue. The system may in specific cases be "ringed" for support.

The same concept of using an arterialized venous access catheter may be applied to the use of long term indwelling catheters used to give chemotherapy etc., making the current ports obsolete as these new access systems will have a decreased thrombosis rate and they will no longer need to be flushed as continuous blood flow through the system makes thrombus formation unlikely. This will definitely cut down on costs since it will decrease nursing requirements in out patient settings, etc.

In alternate embodiments shown in FIGS. 5 and 6, the system comprises an arterial reservoir structure or port 50 with needle accessible top portions 51a and 51b, each of which a preferably-constructed of silicone. The arterial reservoir structure 50 is connected to an outlet tube 53 of PTFE (gortex-ringed), which is sewn to an artery 30 at its other end. The venous outlet tube portion 57 is constructed in a similar way but it is either sewn to a vein 40 via gortex ringed portion 52 or is placed percutaneously into the central circulation via an indwelling venous (silicon) catheter 42 as shown in FIG. 6. There is no continuous flow through this version of the system since the ports are not connected. Flow is established when the system is attached to an HD machine with a needle 15 in the arterial port 51a to deliver blood to the HD machine and a second needle 15 is placed in the venous port 51b to the vein 40 to deliver blood to the patient. The ports 51a, 51b will remain flushed with heparin when not in use to avoid clotting when accessed through the skin 14 with needles 15. The ports 51a, 51b will also provide high flow access to both the arterial and venous systems. FIG. 6 shows two separate ports 51a and 51b with the outlet tube 53 sewn to an artery 30 and the indwelling venous catheter 42 floated down a vein 40.

Figure 7:
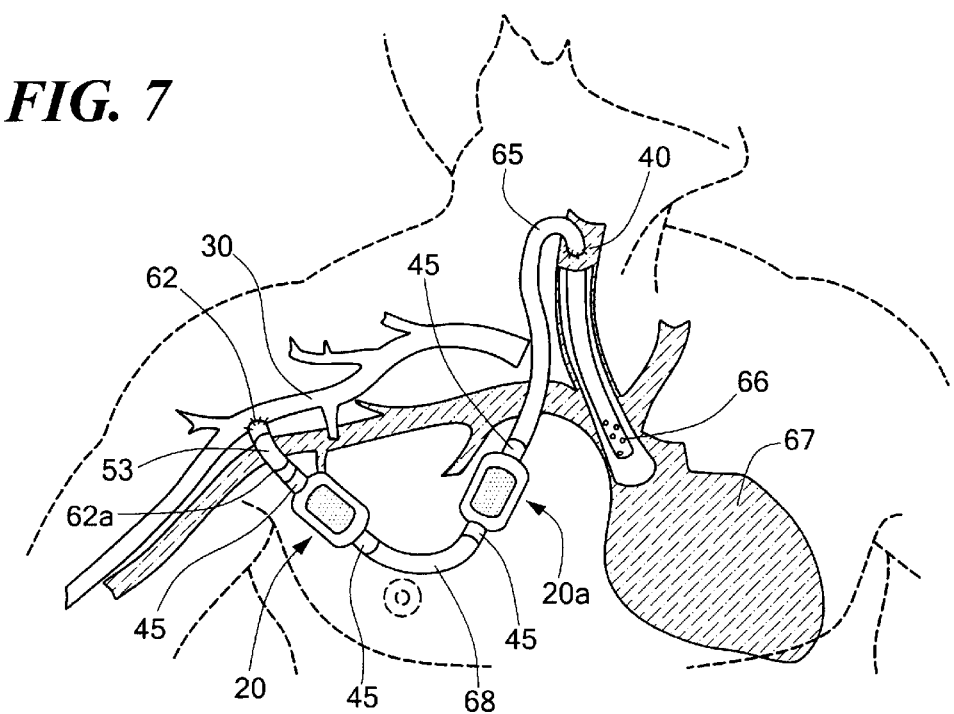
FIG. 7 illustrates a ringed tube sewn to an artery and connected to a first access site which is joined to a second site by silastic tubing and includes an outflow through silastic tubing which is floated into the venous system.

FIG. 7 illustrates, in an anatomical drawing, an outlet tube 53 of PTFE (ringed gortex) sewn to an artery 30 at 62 and coupled at its other end 62a to the needle access site 20. The site 20, see FIGS. 1–3, is joined by silastic tubing 68 to a second access site 20a which has an outlet silastic tube 65. The outlet tube 65 includes a plurality of perforations 66 at its outlet end which is positioned in the venous system 67 through vein 40. Either site 20 or 20a can be used for needle access.

Figure 8:
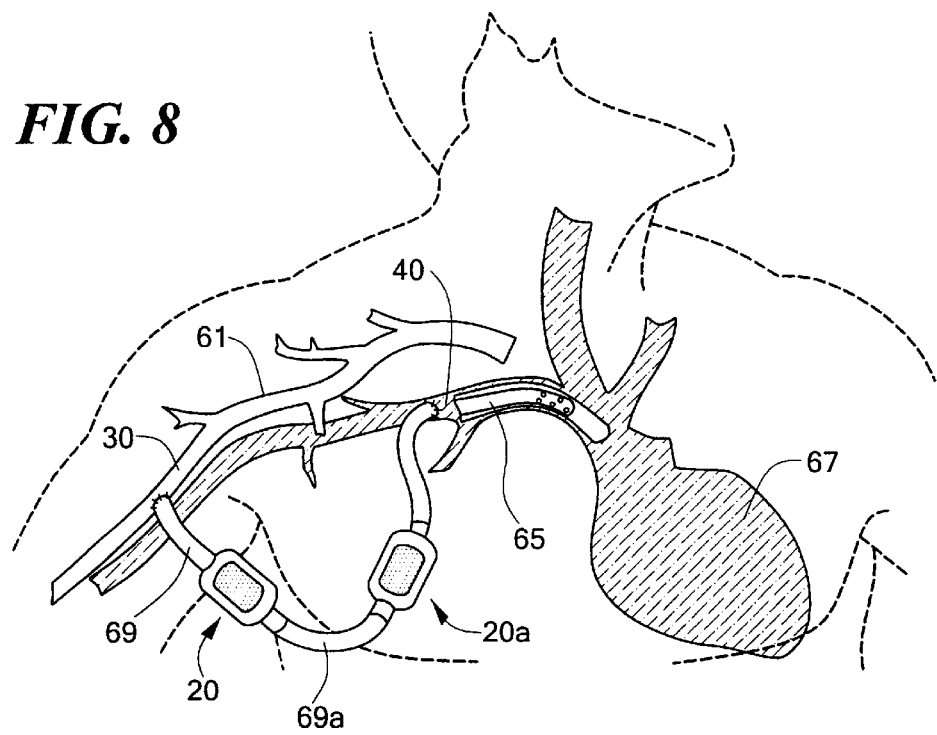
FIG. 8 is similar to FIG. 7 but shows PTFE sewn to an artery and silastic tubing floated into a different portion of the venous system.

FIG. 8 depicts an embodiment similar to that of FIG. 7 except that the coupling between the artery 30 and the first needle access site 20 is PTFE tube 69. The entry to the venous system 67 is via vein 40 which has silastic tubing 65 floated therein. A PTFE tube portion 69a joins parts 20 and 20a.

Figure 9:
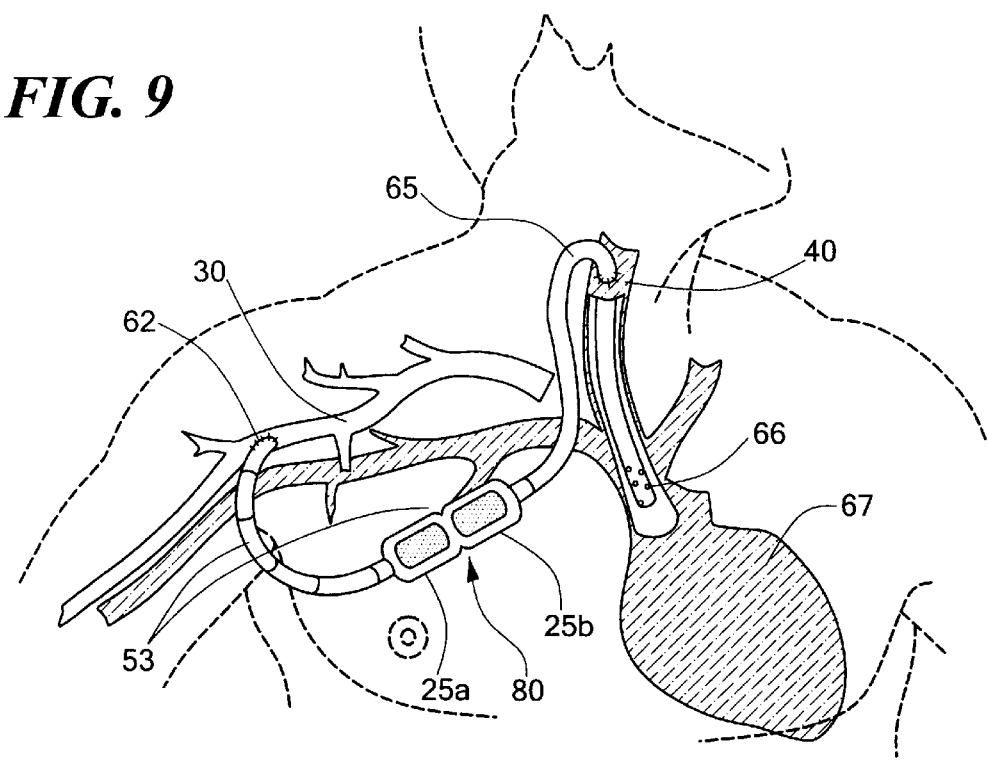
FIG. 9 depicts ringed PTFE tubing sewn to the subclavian artery and a dual access site coupled to the venous system at its other end.

FIG. 9 illustrates a dual needle access site 80 which is coupled via outlet tube 53 of PTFE (gortex-ringed) to the subclavian artery 30 and floated into the venous system 67 via silastic tubing 65. The dual site 80 provides additional access through 25a, 25b in approximately the same area with tubing (not shown) extending through the dual site needle access site 80.

Figure 10:
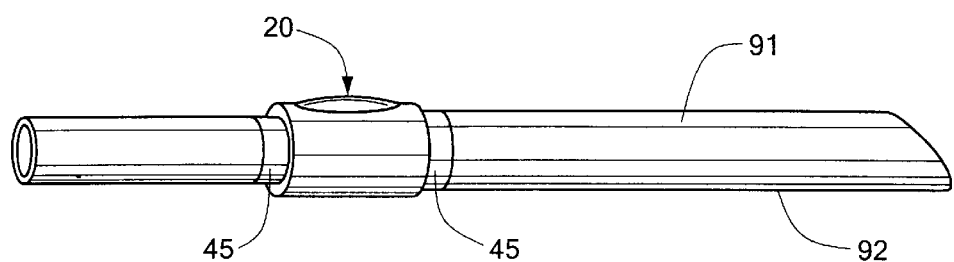
FIG. 10 shows a multi-layered variation at the venous end of the system.

FIG. 10 depicts a variation of the invention at the venous end wherein the outlet of the port 20 comprises PTFE tubing 91 located within a silastic catheter 92. This design is appropriate if thrombosis is a problem in the outlet silastic portion of the shunt.

Figure 11:
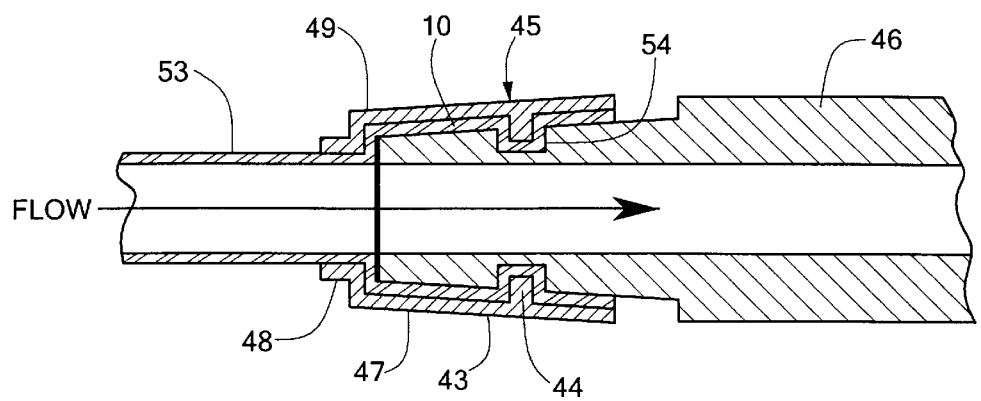
FIG. 11 discloses a quick coupler design utilized in conjunction with the system.

FIG. 11 discloses a quick coupler 45 joining the PTFE outlet tube 53 (gortex-ringed) to the port 46 in the needle access site 20. A plastic or metal member 47 includes a portion 48 which engages the cylindrical PTFE tubing 10, an intermediate portion 49 extending perpendicularly outward and an end portion 43 tapered outwardly at an angle and including an inward projection 44. The projecting portion 44 of the member 47 engages a slot 54 in the port 46 firmly fixing the cylindrical PTFE tubing 10 therebetween. Portion 48 is made of flexible material to allow a gentle curve in tubing as it exits/enters port.

Figure 12:
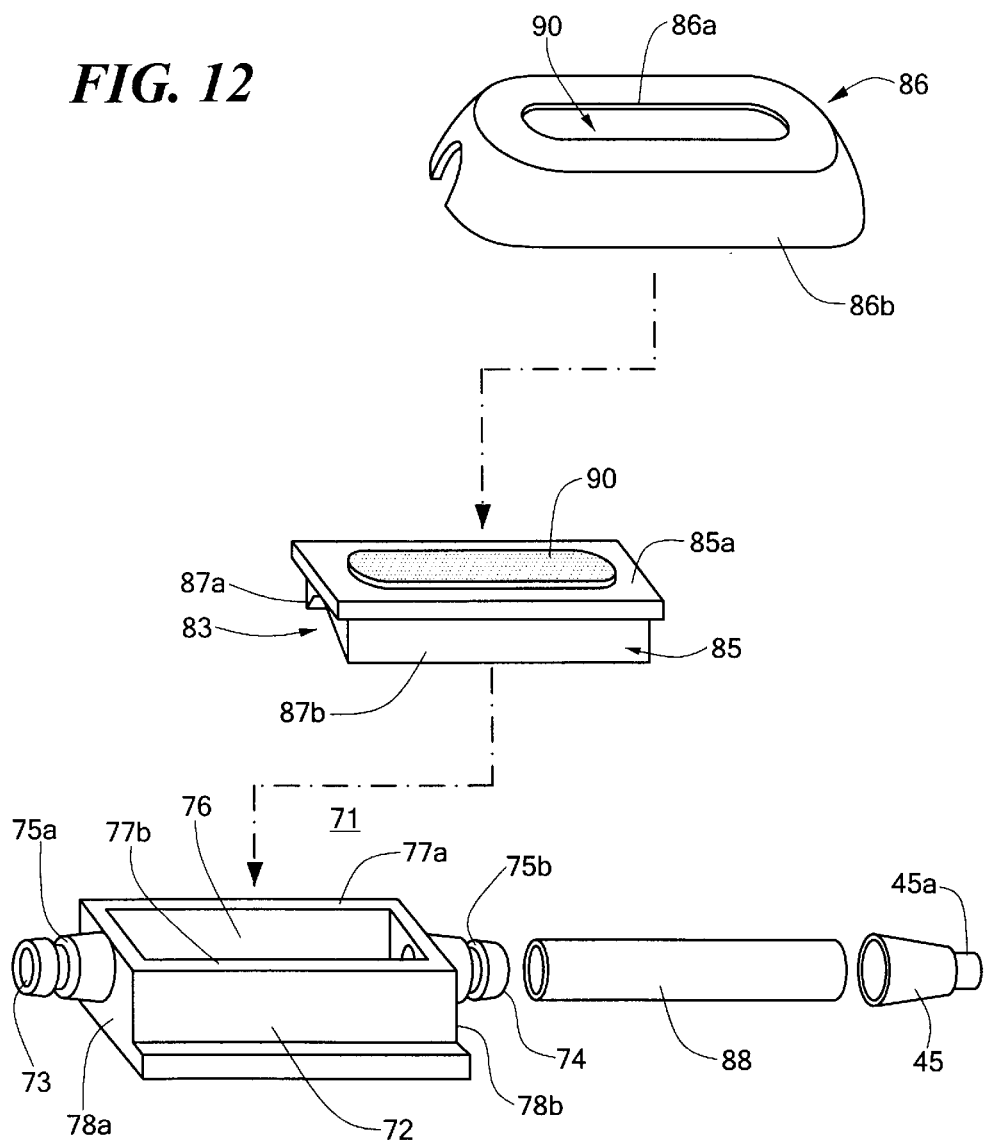
FIG. 12 is a unique port design utilized in conjunction with the system.

FIG. 12 is an exploded view of a new port embodiment wherein the port 71 comprises a frame 72 having an inlet coupling 73 and an outlet coupling 74. The plastic or metal frame 72 includes a recessed reservoir 76 and end walls 78a and 78b. An upper member 85 having a top or upper member 85a, a recess 83 and downwardly projecting sides 87a and 87b fits within walls 77a and 77b. The upper member 85 includes an oval silicone access site 90. The member 45 rapidly couples the PTFE tubing 10 to site 71 with tubing 88 which fits over the inlet coupling 73 and the outlet coupling 74 with recessed portions 75a and 75b which engage tubing 88 (only one of which is shown) and have couplers 45 (only one of which is shown) which slide over the tubing 88 to engage the inlet and outlet couplings 73 and 74.

A housing 86 includes a top portion 86a and a side portion 86b. The top portion 86a includes an aperture which surrounds and provides a means for accessing the oval silicone access site 90. This embodiment provides a quick assembly for a needle access site 71.

Figure 13:
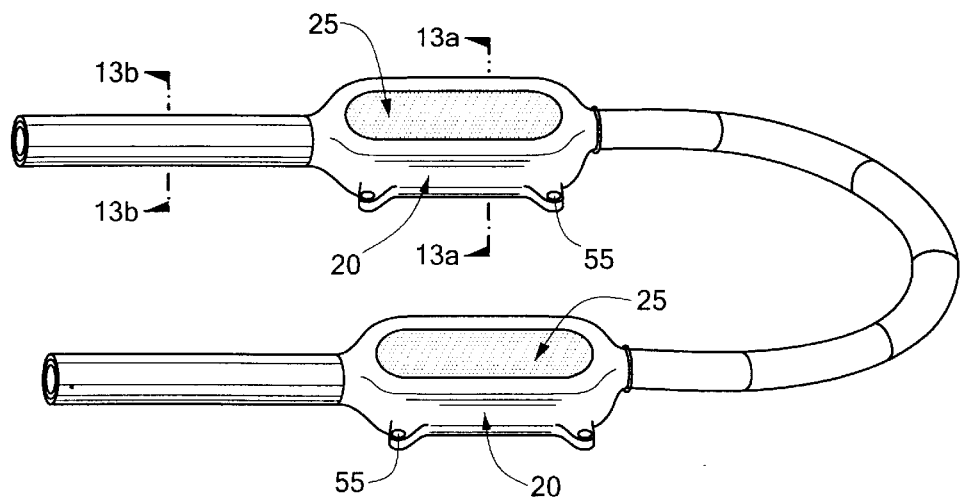
Figure 13A:
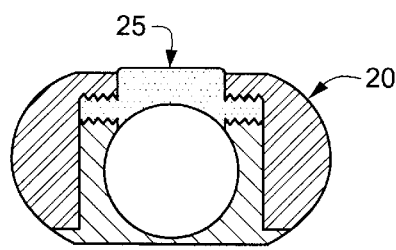
FIG. 13a and FIG. 13b show cross-sectional views which depict the internal construction of the invention with FIG. 13b illustrating multi-layered tubing; and, FIG. 14 shows a variation of the system entry through vein wall (i.e. not percutaneous or purse string) wherein a cuff, sewn to vein as indwelling portion, is floated down stream.
Figure 13B:
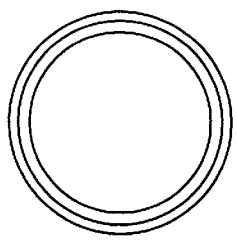

FIG. 13 shows a typical dual port system showing holes 55 where ports 20 can be fixed in place, while FIG. 13a and FIG. 13b show cross-sectional views which depict the internal construction of the invention with FIG. 13b illustrating multi-layered tubing.

Figure 14:
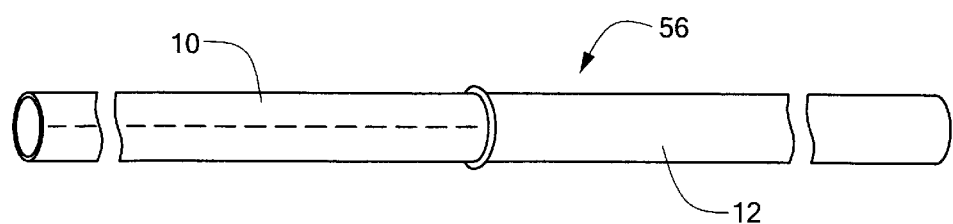

FIG. 14 discloses a cuff 56 which is made of PTFE and sewn to a vein. No physiological/functional venues anastomosis is created as blood is returned at the end of the system distant from the cuff. The silastic end 12 may still be lined with PTFE.

The Squitieri Hemodialysis/Vascular Access System avoids creation of a venous anastomosis, a revolutionary advancement, i.e. there is no site for neointimal hyperplasia at a venous anastomosis which accounts for the vast majority of PTFE arteriovenous graft failures (60–80%). This is accomplished by returning the blood into a larger vein via an indwelling venous catheter 42. The site of blood return to the venous system is not fixed to the vein wall where neointimal hyperplasia occurs with the standard PTFE bridge graft. This feature represents a tremendous advantage over the present grafts.

As a further advantage, the system is not stagnant and prone to thrombosis, i.e. constant flow through the new system avoids the problem of clotting inherent in indwelling dual lumen venous catheters which remain stagnant when not in use. It also avoids need to flush catheters with heplock thereby reducing nursing costs to maintain the catheter.

The Squitieri system avoids externalization of components which are prone to infection. Since dual lumen catheters exit the skin 14, they frequently lead to sepsis requiring catheter removal despite subcutaneous tunneling. This new access is entirely subcutaneous.

Very importantly the system proposed herein, avoids problems with the aspiration of blood from the venous system and "positional" placement through continuous flow. A frequent problem with dual lumen catheters is their inability to draw blood from the venous system due to clot and fibrinous debris ball-valving at the tip of a catheter. This new system receives blood directly from arterial inflow which ensures high flow rates needed for shorter, more efficient dialysis runs. It also avoids the frequent problem of the catheter tip "sucking" on the vein wall inhibiting flow to the dialysis machine and rendering the access ineffective.

The system avoids recirculation seen with dual lumen catheters resulting in more efficient and more cost effective dialysis.

The system avoids the need for temporary access with incorporation of "Needle Access Sites" 20. A-V fistulas and gortex grafts must "mature" for several weeks before use. This creates a huge strain on the patient as well as the doctor to achieve temporary access while waiting to use the permanent access. Temporary access is very prone to infection, malfunction and vein destruction. By placing sites 20 designed to receive needles 15 along the new access, the system may be used the day it is inserted.

The system avoids PTFE needle site damage with the incorporation of "Needle Access Sites" 20. Needle access directly into PTFE is presently uncontrolled and user dependent. Often, PTFE is lacerated by access needles. While this system may be accessed via the PTFE segment, the needle receiving sites are the preferred method. This leads to excessive bleeding which requires excessive pressure to halt the bleeding causing thrombosis of the graft. "Needle Access Sites" 20 on the Squitieri access system allow safe, quick, and easy entry into the system and avoid the complications inherent in placing needles directly into PTFE. It also avoids perigraft bleeding which will compress and thrombose the graft. By eliminating the long time needed to compress bleeding at the needle site, the system shortens dialysis runs.

The Squitieri system permits an easier, faster insertion technique. Only one anastomosis the arterial end and a percutaneous placement of the venous end is required. A modification allows the system to be sutured to the vein wall while the system tubing is floated down stream from this site where the system enters the vein 40. This saves operating room time at thousands of dollars per hour. The technique is easier with faster replacement. It avoids difficult and time consuming revision of venous anastomosis required to repair venous outflow occluded by neointimal hyperplasia. If the system malfunctions, the silastic catheter end 65 slips out easily and the arterial end of the outlet tube 53 is thrombectomized. New access sewn to the thrombectomized end of the outlet tube 53 of PTFE at the arterial end and the silastic venous end is replaced percutaneously via Seldinger technique or "open technique".

The end result of the above advantages translates into superior patency rates and a decreased complication rate with this new system. Patients are spared the repeated painful hospitalizations for failed access as well as the emotional trauma associated with this difficult condition. The physicians are spared the dilemma of how to best treat these patients. This system will have a large impact on the current practice of vascular access in areas such as hemodialysis; plasmapheresis; chemotherapy; hyperalimentation; and chronic blood draws.

While the invention has been explained by a detailed description of certain specific embodiments, it is understood that various modifications and substitutions can be made in any of them within the scope of the appended claims which are intended also to include equivalents of such embodiments.

What is claimed is:

1. A hemodialysis and vascular access system comprising:
   a catheter having a graft section and a catheter section wherein:
      said graft section is provided from a material which is adapted for long term attachment to an artery with a first portion of said graft section adapted to be coupled to an artery; and
      said catheter section has a first portion adapted to be inserted within a vein at an insertion site, with an end or the first portion having an opening adapted to be within the vein itself and wherein the opening in the end of the first portion of said catheter section is distant from the insertion site and wherein the first portion of the catheter section is provided having an outer diameter which is less than an inner diameter of the vein in which the first portion if the catheter section is adapted to be disposed such that, in operation, blood can flow through the first portion of the catheter section into the vein and through the vein around an outer surface of the first portion of said catheter section.

2. The hemodialysis and vascular access system of claim 1, wherein a second portion of said graft section is adapted to be coupled to a second portion of said catheter section and wherein said graft and catheter sections are coupled such that fluid is able to flow from the graft section to the catheter section.

3. The hemodialysis and vascular access system of claim 1 wherein said graft section is provided from a first tube and said catheter section is provided from a second tube with a second end of said first tube coupled to a second end of said second tube.

4. The hemodialysis and vascular access system of claim 3 wherein at least one of said first and second tubes are adapted for percutaneous placement.

5. The hemodialysis and vascular access system of claim 3 wherein the first end of said second tube includes an enlarged portion in which the first end of said first tube is disposed.

6. The hemodialysis and vascular access system of claim 3 wherein the first end of said first tube includes an enlarged portion in which the first end of said second tube is disposed.

7. The hemodialysis and vascular access system of claim 3 wherein said first tube comprises multiple layers.

8. The hemodialysis and vascular access system of claim 1 wherein the first portion of said catheter section is adapted to be floated within a vein and is provided from a material which is bendable such that when the first portion of said catheter section is disposed within the vein, it is displaced from an inner surface of the vein.

9. The hemodialysis and vascular access system of claim 8 wherein the first portion of said catheter section is adapted to be coupled to the vein wall.

10. The hemodialysis and vascular access system of claim 8 wherein the first portion of said catheter section is not adapted to be coupled to the vein wall.

11. The hemodialysis and vascular access system of claim 1 wherein said graft section is provided from a material which is biocompatible with an artery and which has a nonthrombogenic characteristic.

12. The hemodialysis and vascular access system of claim 11 further comprising a region for repeated needle access.

13. The hemodialysis and vascular access system of claim 1 wherein a side region of the first portion of said catheter is provided having at least one opening therein.

14. The hemodialysis and vascular access system of claim 13 wherein each of the at least one openings in the side region of the first portion of said catheter are positioned such that each of the at least one openings in the side region are adapted to be within the vein itself and each of the at least one opening is distant from the insertion site.

15. The hemodialysis and vascular access system of claim 1 wherein the end of said second tube which is coupled to the first tube includes an enlarged portion in which the first end of said first tube is disposed.

16. The hemodialysis and vascular access system of claim 1 wherein the first portion of the catheter section is provided having an inner diameter and a length adapted to be disposed within the vein selected such that blood from the artery flows through the graft section and enters the flow of blood in the vein in a direction which is substantially parallel to a direction of blood flow in the vein.

17. The hemodialysis and vascular access system of claim 1 wherein the outer diameter of the wall in the first portion of said catheter section which defines the opening in the end of the first portion of said catheter section is less than an inner diameter of the vein in which the first portion of said catheter section is disposed.

18. The hemodialysis and vascular access system of claim 1 wherein the graft section of said catheter is provided from a graft material and the catheter section of said catheter is provided from a catheter material which is different than the graft material.

* * * * *

UNITED STATES PATENT AND TRADEMARK OFFICE
CERTIFICATE OF CORRECTION

PATENT NO. : 6,582,409 B1  Page 1 of 1
DATED : June 24, 2003
INVENTOR(S) : Rafael Squitieri It is certified that error appears in the above-identified patent and that said Letters Patent is hereby corrected as shown below:

Column 2,
Lines 19, 20 and 27, delete "i.e." and replace with -- i.e., --.

Column 3,
Line 5, delete "i.e." and replace with -- i.e., --.
Line 18, delete "a unique" and replace with -- unique --.

Column 4,
Line 3, delete "down stream" and replace with -- downstream --.
Lines 17 and 39, delete "in line" and replace with -- in-line --.
Line 30, delete "catheter" and replace with -- catheter, --.
Line 33, delete "blood stream" and replace with -- bloodstream --.
Line 53, delete "exchangability" and replace with -- exchangeability --.

Column 5,
Line 34, delete "out patient" and replace with -- outpatient --.
Line 39, delete "which a preferably" and replace with -- which are preferably --.

Column 6,
Line 62, delete "i.e." and replace with -- i.e., --.

Column 7,
Line 5, delete "i.e." and replace with -- i.e., --.
Line 58, delete "down stream" and replace with -- downstream --.

Signed and Sealed this

Sixteenth Day of September, 2003

JAMES E. ROGAN
*Director of the United States Patent and Trademark Office*